United States Patent [19]
Jacobs

[11] Patent Number: 5,459,700
[45] Date of Patent: Oct. 17, 1995

[54] MANUAL TIMER CONTROL FOR INFLATION DEVICE

[75] Inventor: James M. Jacobs, Mountain View, Calif.

[73] Assignee: Advanced cardiovascular Systems, Inc., Santa Clara, Calif.

[21] Appl. No.: 156,253

[22] Filed: Nov. 22, 1993

[51] Int. Cl.$^6$ .......................... G04B 47/00; A61M 29/02
[52] U.S. Cl. ............................... 368/10; 368/113; 604/97; 604/100; 606/194
[58] Field of Search .............................. 368/10, 110–113; 604/96–103; 606/192–196

[56] References Cited

U.S. PATENT DOCUMENTS

| | | |
|---|---|---|
| 3,623,474 | 11/1971 | Heilman . |
| 3,698,381 | 10/1972 | Federico et al. . |
| 3,701,345 | 10/1972 | Heilman et al. . |
| 3,720,199 | 3/1973 | Rishton et al. . |
| 4,006,736 | 2/1977 | Kranys et al. . |
| 4,106,002 | 8/1978 | Hogue, Jr. . |
| 4,321,014 | 3/1982 | Eburn, Jr. et al. . |
| 4,332,254 | 6/1982 | Lundquist . |
| 4,370,982 | 2/1983 | Reilly . |
| 4,439,185 | 3/1984 | Lundquist . |
| 4,439,186 | 3/1984 | Kuhl . |
| 4,493,704 | 1/1985 | Beard et al. . |
| 4,576,181 | 3/1986 | Wallace et al. . |
| 4,583,917 | 4/1986 | Shah . |
| 4,583,974 | 4/1986 | Kokernak . |
| 4,608,994 | 9/1986 | Ozawa et al. . |
| 4,610,256 | 9/1986 | Wallace . |
| 4,651,738 | 3/1987 | Demer et al. . |
| 4,654,027 | 3/1987 | Dragan et al. . |
| 4,655,749 | 4/1987 | Fischione . |
| 4,677,980 | 7/1987 | Reilly et al. . |
| 4,677,982 | 7/1987 | Llinas et al. . |
| 4,694,409 | 7/1987 | Lehman . |
| 4,723,938 | 2/1988 | Goodin et al. . |
| 4,743,230 | 5/1988 | Nordquest . |
| 4,758,223 | 7/1988 | Rydell . |
| 4,781,192 | 11/1988 | Demer . |
| 4,795,431 | 1/1989 | Walling . |
| 4,796,606 | 1/1989 | Mushika . |
| 4,808,165 | 2/1989 | Carr . |
| 4,832,692 | 5/1989 | Box et al. . |
| 4,838,864 | 6/1989 | Peterson . |
| 4,854,324 | 8/1989 | Hirschman et al. . |
| 4,911,695 | 3/1990 | Lindner . |
| 4,919,121 | 4/1990 | Rydell et al. . |
| 4,929,238 | 5/1990 | Baum . |
| 4,940,459 | 7/1990 | Noce . |
| 4,944,726 | 7/1990 | Hilal et al. . |
| 4,952,928 | 8/1990 | Carroll et al. . |
| 4,985,015 | 1/1991 | Obermann et al. . |
| 5,004,472 | 4/1991 | Wallace . |
| 5,007,904 | 4/1991 | Densmore et al. . |
| 5,009,662 | 4/1991 | Wallace et al. . |
| 5,015,233 | 5/1991 | McGough et al. . |
| 5,019,041 | 5/1991 | Robinson et al. . |
| 5,021,046 | 6/1991 | Wallace . |
| 5,047,015 | 9/1991 | Foote et al. . |
| 5,057,078 | 10/1991 | Foote et al. . |
| 5,084,060 | 1/1992 | Freund et al. . |
| 5,135,488 | 9/1992 | Foote et al. . |
| 5,1,52,776 | 10/1992 | Pinchuk . |
| 5,163,904 | 11/1992 | Lampropoulos et al. . |
| 5,201,753 | 4/1993 | Lampropoulos et al. . |
| 5,215,523 | 6/1993 | Williams et al. . |
| 5,273,537 | 12/1993 | Haskvitz et al. . |
| 5,300,027 | 4/1994 | Foote et al. . |

FOREIGN PATENT DOCUMENTS

| | | |
|---|---|---|
| WO90/04987 | 5/1990 | WIPO . |
| WO90/11040 | 10/1990 | WIPO . |
| WO92/06735 | 4/1992 | WIPO . |
| WO92/15359 | 9/1992 | WIPO . |

*Primary Examiner*—Vit W. Miska
*Attorney, Agent, or Firm*—Fulwider Patton Lee & Utecht

[57] ABSTRACT

A manually operable pressure switch is used to activate an inflation device in order to pressurize an inflatable member such as that found on a dilatation catheter. By operating the pressure switch, the physician simultaneously operates a timer which will measure and display the elapsed time of the inflation and deflation cycle.

13 Claims, 1 Drawing Sheet

MANUAL TIMER CONTROL FOR INFLATION DEVICE

BACKGROUND OF THE INVENTION

This invention generally relates to inflation devices used in medical procedures. More particularly, the present invention pertains to an inflation timing system suitable for inflating and deflating catheter balloons used in vascular procedures such as angioplasty performed on a patient for maintaining the patency of a blood vessel.

Dilatation balloon catheters have been used in increasing numbers in angioplasty procedures to dilate or enlarge blood vessels that have been partially or almost completely blocked by stenosis (a narrowing of the vessel due to injury or disease). Angioplasty procedures have been used to treat stenoses in coronary arteries, peripheral arteries, urethral passages, fallopian tubes, etc. Particularly, the procedure for dilating coronary arteries, referred to as percutaneous transluminal coronary angioplasty (PTCA), has provided an effective and less traumatic treatment technique than coronary by-pass surgery or other surgical treatment methods.

In a typical PTCA procedure, a guiding catheter is percutaneously introduced into the vascular system of a patient and is directed to a point near the site of the occlusion. Subsequently, a guidewire and a dilatation catheter having an inflatable balloon on the distal end thereof are introduced through the guiding catheter with the guidewire slidably disposed within an inner lumen of the dilatation catheter (commonly referred to as an over-the-wire system). The guidewire is advanced out of the distal end of the guiding catheter and is maneuvered into the patient's vasculature containing the lesion to be dilated, and is then advanced beyond the lesion. Thereafter, the dilatation catheter is advanced over the guidewire until the dilatation balloon is located across the lesion. Once in position across the lesion, the balloon of the dilatation catheter is filled with radiopaque liquid at relatively high pressures (e.g., generally greater than about 4 atmospheres) and is inflated to a predetermined size, preferably the same as the inner diameter of the artery at that location. The inflated balloon radially compresses the atherosclerotic plaque of the lesion against the inside of the artery wall to thereby dilate the lumen of the artery and allow blood to flow freely therethrough. In a typical PTCA procedure, the balloon may be inflated and deflated several times, with the pressure maintained for a short duration, i.e., typically three minutes or less during each inflation, until the desired patency in the blood vessel is obtained. The balloon is then deflated so that the dilatation catheter can be removed and blood flow resumed through the dilated artery. The above PTCA procedure also can be performed using a fixed-wire system or a rapid exchange guidewire system.

To inflate or deflate the balloon, the physician typically uses an inflation system such as a syringe placed in fluid communication with the interior of the balloon. The physician uses one hand to grasp the syringe body and the other hand to maneuver the plunger to pressurize the inflation fluid. Syringe-type inflation systems of the type described are manufactured and sold by Advanced Cardiovascular Systems, Inc. of Santa Clara, Calif. under the trademark INDEFLATOR.

There are some drawbacks associated with a manual inflation procedure such as the one described. For example, each time the physician wants to adjust or change the location of the balloon in the artery, she must use her hand alternatingly on the proximal end of the catheter for maneuvering the balloon to the desired location and on the inflation device for pressurizing or depressurizing the balloon. Rather than switching hands between the balloon catheter and the inflation device, it is desirable for the physician to be able to simultaneously control the inflation pressure and the location of the balloon in the artery. Another drawback of manual inflation systems is that the physician may experience hand fatigue as a result of operating an inflation device for several inflation and deflation cycles during an angioplasty procedure. Additionally, manual inflation devices are often bulky, especially compared with the size of a dilatation balloon catheter which is small and delicate. The presence of a bulky inflation device is preferably to be avoided in the immediate area of a balloon dilatation catheter so that the physician retains the proper "feel" of the catheter without interference from the weight and size of the inflation device.

In addition to the above concerns, it is desirable for the physician performing an angioplasty procedure to monitor the balloon pressure and the time of the inflation and deflation cycles. A balloon pressure display allows the physician to monitor whether the arterial plaque causing the stenosis is subjected to a sufficiently high pressure to cause compression of the plaque. Also, the physician would like to monitor the balloon pressure to estimate the resultant diameter of the balloon, and to ensure that the balloon pressure limits specified by the manufacturer are not exceeded so as to cause a balloon failure. In case the balloon pressure suddenly changes, the pressure display can alert the physician of the possibility of some failure either of the artery or of the catheter itself. Furthermore, it is desirable for the physician to monitor the elapsed time of each inflation and deflation cycle and the total inflation and deflation times so as not to deprive the patient of blood flow inside the artery beyond acceptable time periods. Early model inflation systems provided balloon pressure measurements by utilizing analog pressure gauges to correlate the force applied on the inflation device with the pressure inside the balloon.

In recent years, various inflation devices have become known which are able to instantaneously monitor, display, and record balloon pressure values and inflation times. Other advances in the design of inflation systems have been directed to creating automated inflation devices, whereby a microprocessor provides control signals to a drive unit which advances or retracts a syringe for the purpose of inflating or deflating a balloon catheter. The microprocessor can be made to follow a predetermined output pattern based on the inflation pressure detected by the pressure transducer and the time of inflation, or it can be designed for manual activation by control switches that are typically mounted on the same unit that displays the pressure and time values. Some of the automated inflation devices include a floor switch for operating a control unit to inflate and deflate the balloon. There are some disadvantages in connection with floor switches, such as the possibility of activation of the control unit by catheter lab personnel who may inadvertently step on the floor switch.

Further, such inflation devices reduce the hands-on control of a physician who may desire to inflate or deflate the balloon catheter at a precise moment during the maneuvering of the catheter in the artery. Activation of control switches that are typically mounted away from the balloon catheter requires the physician to give up control of the proximal end of the catheter in order to activate the control switches. Thus, existing inflation systems do not lend themselves to simultaneous activation of the inflation device and timing controls by the physician.

Another important step that takes place in a typical angioplasty procedure is the priming of the inflation system and the prepping of the balloon. The physician performing an angioplasty procedure must rid the inflation system and the balloon from air bubbles before the insertion of the catheter inside the patient's vasculature. If the system is not primed and prepped, these air bubbles enter the inflation lumen of the catheter and create unwanted pockets of space in the balloon that may interfere with the balloon inflation. Current methods of priming are well known in the art by angioplasty practitioners, and typically require the physician to manually inflate and deflate the system several times until the air bubbles disappear. After the priming function has been completed, the pressure in the inflation lumen and the inflation balloon may be less than zero. Thus, when an automatic pressure measuring device is used in conjunction with a timer, false or inaccurate inflation times (artifactual inflation) might be recorded since the balloon pressure starts out at a negative pressure.

What has been needed and heretofore unavailable is a simplified automated inflation system that enables the physician to effectively, easily, and simultaneously control and monitor the inflation pressure and the inflation and deflation time of the balloon member. Such an inflation system would be able to easily interface with commercially available dilatation balloon catheters, and would eliminate the need for having bulky components of an inflation system in the immediate area of an angioplasty procedure. Also, such an automated inflation system would be able to monitor and display information relating to balloon pressure and inflation times.

SUMMARY OF THE INVENTION

The invention is directed to an inflation/deflation system that more accurately measures the elapsed time of the inflation and deflation cycle of a medical procedure using a catheter and displays the elapsed time on a monitor so that the physician can monitor the duration of the procedure.

The present invention allows the physician to manually operate a pressure switch which activates a timer for timing the inflation and deflation cycle. In activating the pressure switch, the physician activates an inflation device which will pressurize and inflate the balloon portion of the catheter. After an inflatable member or balloon is inflated, deactivation of the pressure switch simultaneously activates the timer to measure the elapsed time of the inflation and deflation cycle. A display monitor provides a constant readout of the elapsed time allowing the physician to carefully monitor the time the inflated balloon is blocking a coronary artery or other vessel in the body. The timer generally will stop when the pressure in the balloon falls below a pre-set amount, preferably zero atmospheres pressure.

The timer can be manually operated to start based on the physician's operation of a pressure switch. Certain safety features are provided so that the elapsed time displayed to the physician is accurate. For example, the timer automatically stops when the fluid pressure drops below a pressure threshold, usually at zero atmospheres. Also, in order to eliminate artifactual inflation, the timer is disabled when the measured pressure is less than a very low threshold pressure which would not inflate a balloon.

The timer can include a processor control routine which controls timing of the inflation cycle according to the manual control of the pressure switch. In one embodiment, the inflation timing does not begin until the "increase-pressure" switch is released after having been depressed. In typical cath lab situations, the balloon portion of the catheter will be under slightly negative pressure after being prepped, i.e., near minus one atmospheres to begin. When the increase-pressure button is activated, pressure in the balloon increases and, after exceeding zero atmospheres (or some other user set value such as one-half or one atmosphere), a release of the increase-pressure button will cause the timer to begin timing inflation. The timer will continue to measure the elapsed time until the pressure in the system has returned to zero atmospheres.

The inflation/deflation system includes a fluid chamber having a plunger for pressurizing a body of inflation fluid in response to the motion of the plunger that is caused by an electromechanical motor drive unit. Upon the movement of the plunger inside the fluid chamber, the inflation fluid is directed inside the inflation lumen of a balloon catheter via a tubing that runs between the fluid chamber and the catheter inflation lumen. The tubing is of a suitable strength to withstand inflation pressures experienced in vascular procedures. As the catheter inflation lumen is open to the interior of the balloon, the inflation fluid ultimately inflates the balloon which in turn causes compression of the plaque or other obstruction against the interior wall of the patient's vessel. The deflation of the balloon takes place by rapidly reversing the movement of the motor drive unit so as to withdraw the inflation fluid from the interior of the balloon and maintain it back inside the fluid chamber. In order to make it possible for the physician to depressurize the balloon in case of any failures of the motor drive unit or other parts of the inflation system, the fluid chamber is designed so that it may be manually withdrawn from the system by the physician. Also, the plunger is designed so that it can be grasped by the physician and withdrawn from the fluid chamber to create a vacuum.

For ease of access and control by the physician or lab assistant, the pressure switch is preferably mounted on the tubing adjacent the proximal end of the balloon catheter. This feature allows the physician to manipulate the proximal end of the catheter as well as for effecting the inflation or deflation of the balloon and timing the inflation and deflation cycles. Thus, increased accessibility to the pressure switch greatly facilitates the physician's task in positioning and inflating the balloon region of the catheter at the site of the stenosis or obstruction. Also, the improved accessibility of the pressure switch allows the physician to effectuate a rapid deflation of the balloon whenever necessary.

The inflation/deflation system provides the ability to monitor the balloon pressure and the duration of the inflation. For this purpose, a pressure transducer is placed in fluid communication with the inflation fluid, and communicates a signal that is indicative of the balloon pressure to a display unit. The display unit may also display the duration of each inflation and the total cumulative inflation time. The display unit may be located at any convenient location adjacent to the patient.

These and other advantages of the invention will become more apparent from the following detailed description thereof when taken in conjunction with the accompanying exemplary drawings.

DETAILED DESCRIPTION OF THE PREFERRED EMBODIMENTS

Figure 1:
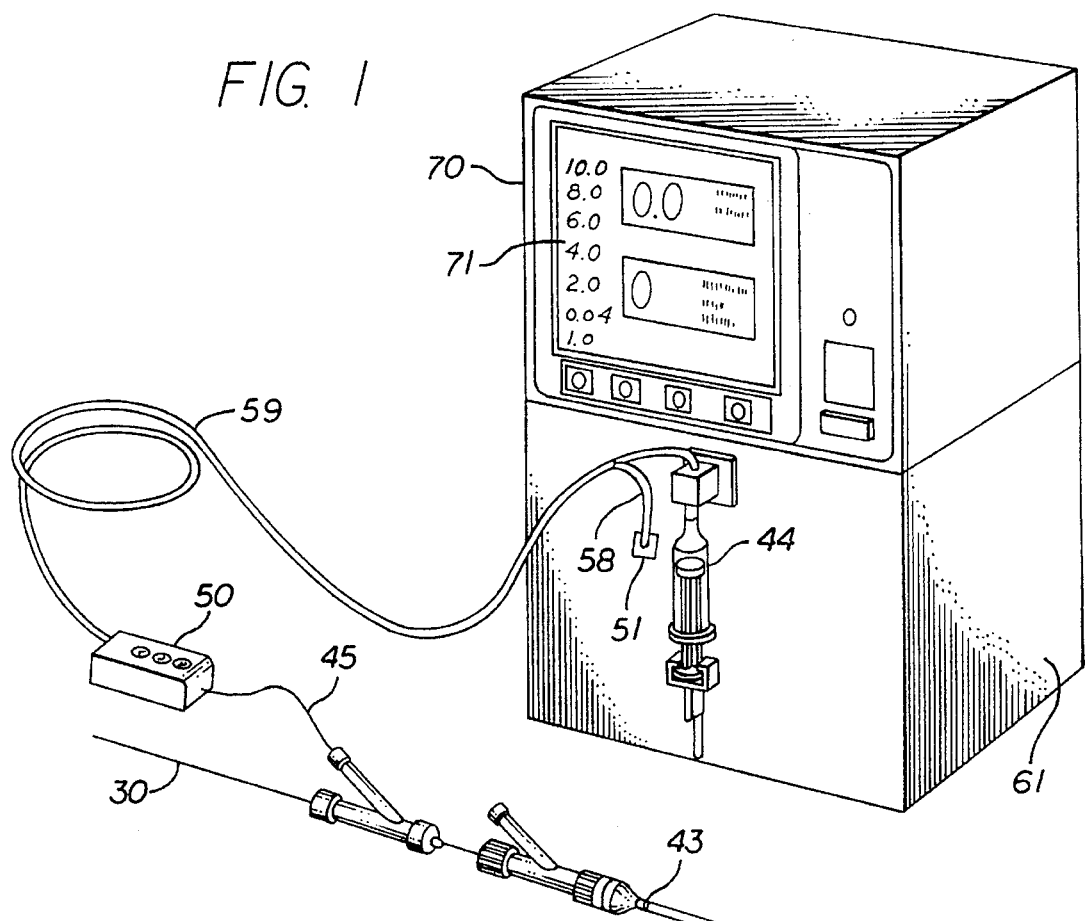
FIG. 1 is a schematic drawing of an inflation/deflation system embodying features of the invention.

In a typical PTCA procedure, a guiding catheter 10 is percutaneously introduced into the vascular system of a patient and is directed to point near the site of an occlusion. In an over-the-wire system 20, as depicted in FIG. 1, a guidewire 30 is inserted into guiding catheter 10 and positioned in the coronary arteries until its distal tip 31 is located past an occlusion or the stenosed area. A dilatation catheter 40 is then threaded over guidewire 30 and it follows the guidewire to the occluded artery. The dilatation catheter 40 will have one or more inflatable members (inflatable balloon) 41 on or near the distal end 42 of catheter 40. As is known in the art, inflatable member 41 is positioned across the occlusion and is inflated one or more times to restore the free flow of blood in the patient's artery. Examples of dilatation catheters and guidewires are found in U.S. Pat. Nos. B1 4,323,071 (Simpson et al.); 4,323,071 (Simpson et al.); 4,439,185 (Lundquist); 4,743,230 (Nordquest); and Re. 33,166 (Samson), which are incorporated by reference herein in their entirety. Such dilatation catheters and PTCA procedures can include other means to carry out the present invention such as use of a fixed wire or rapid exchange dilatation catheter. Examples of such dilatation catheters can be found in U.S. Pat. Nos. Re. 33,166 (Samson) and 5,040,548 (Yock), which are incorporated by reference herein in their entirety.

In PTCA procedures of the type described herein, it is important for the treating physician to know precisely when inflatable member 41 is inflated and when it is completely deflated. When fully inflated, inflatable member 41 completely blocks the artery at the point of occlusion 11 so that blood flow down stream of the inflatable member stops completely. Without proper timing of the inflation and deflation cycle, the patient can be seriously injured.

Figure 2:
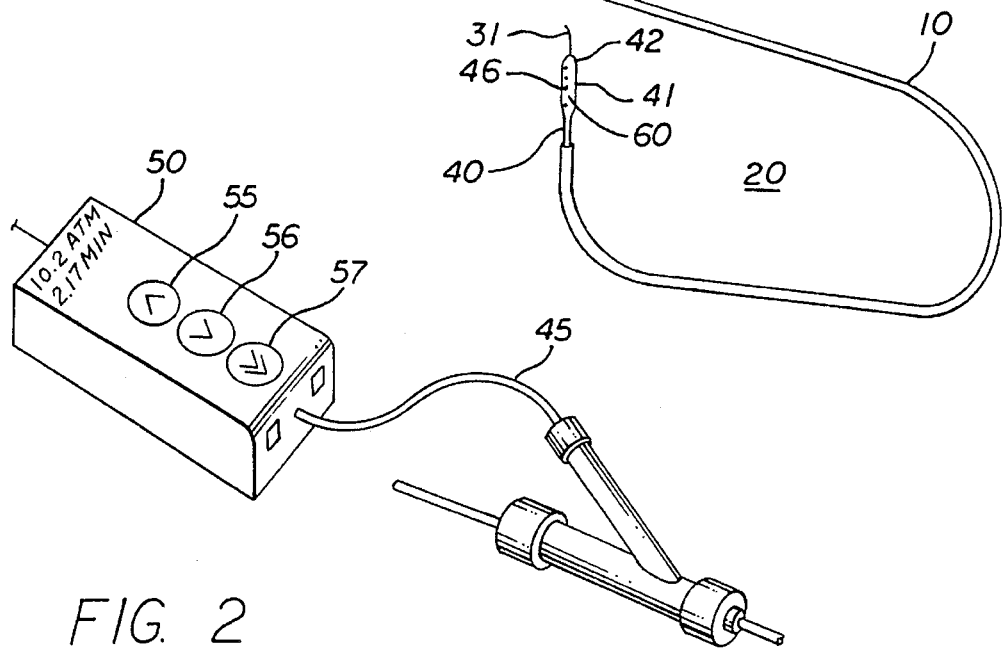
FIG. 2 is a schematic of the pressure switch of the inflation/deflation system shown in FIG. 1, mounted adjacent the proximal end of the catheter, and incorporating a display unit for displaying balloon pressure and inflation times.

Referring to FIGS. 1 and 2, and in keeping with the invention, dilatation catheter 40 has a proximal end 43 which has an inflation device 44 attached thereto. The inflation device is in fluid communication with inflatable member 41 through inflation lumen 45.

A manually operable pressure switch 50 is used to activate inflation device 44 thereby pressurizing inflation lumen 45 and inflatable member 41. The physician manually operates pressure switch 50, which is positioned on catheter 40 near its proximal end 43, to begin pressurizing inflation member 41. Pressure switch 50 is positioned so that the physician can easily operate the switch and maneuver the proximal end 43 of catheter 40. In PTCA procedures, the "feel" of the catheter as it is positioned across the lesion and the subsequent inflation of inflatable member 41 is very important. It is therefore advantageous to position pressure switch 50 near the proximal end of the catheter so the physician can use one hand to maintain the "feel" of positioning and inflating while simultaneously activating pressure switch 50 and inflation device 44.

The pressure switch 50 can include three buttons, increase-pressure button 55, decrease-pressure button 56, rapid decrease-pressure button 57. Pressure switch 50 has an electrical cable 58 running to it, and fluid line 59 running through it. At the distal end of switch 50, fluid line 59 extends approximately eighteen inches and has a connection at its end. While any convenient length is suitable, eighteen inches has been selected so that it can be located fairly close to the angioplasty catheter and yet have sufficient length so the physician can have a technical assistant use the switch while the physician handles the catheter.

In one form of operation, pressure-increase button 55 is released, after initially being depressed, to pressurize inflatable member 41. Releasing pressure-increase button 55 initiates inflation timer 51. As the pressure is increased in inflatable member 41 by operation of inflation device 44, the occlusion in the artery is compressed against the arterial wall to provide a larger lumen for increased blood flow. After a short period of time, usually three minutes or less, rapid pressure-decrease button 57 is depressed to decrease pressure in inflatable member 41. When the pressure in inflatable member reaches zero atmospheres, inflation timer 51 stops measuring the elapsed time of the inflation cycle, and begins measuring the elapsed time of the deflation cycle.

In one embodiment of the invention, pressure switch 50 is equipped with a safety feature so that timing of the inflation of inflatable member 41 does not commence until the measured pressure is equal to or greater than atmospheric pressure or a pressure selected by the user. When the catheter is first prepared, a procedure is used to remove air from the system which can leave a negative pressure in the system near minus one atmospheres. Thus, a pressure sensor 60 will monitor pressure in inflatable member 41 and relay that information to process control unit 61 by a pressure signal. The measured pressure signal is compared to a set point, usually atmospheric pressure, and when the measured pressure is equal to the atmospheric pressure, a signal is generated to activate inflation timer 51. This procedure eliminates artifactual inflation which can distort the actual inflation time causing serious harm to the patient. Process control unit 61 is a closed loop feedback control circuit of the type that is well known in the art and that can operate in either an analog or digital mode.

In another embodiment, a processor control routine controls timing of the inflation according to the manual control of the pressure switch. According to the invention, the inflation timing does not begin until the increase-pressure switch 55 is released after having been depressed. Typically, the catheter will be under slightly negative pressure; e.g., minus one atmospheres to begin. After the balloon has been positioned as desired, the physician will then normally press the increase-pressure button 55 on the control switch to cause inflation device 44 to increase fluid pressure in fluid line 59 connected to inflatable member 41. After exceeding zero (0) atmospheres, or some other pre-set threshold pressure, a release of increase-pressure button 55 will cause timer 51 to begin timing the inflation sequence. The timer 51 will continue to time inflation until the pressure in the system has returned to zero (0) atmospheres or the pre-set threshold pressure.

In yet another embodiment, a release of increase-pressure button 55 causes inflation timer 51 to begin. However, if the pressure in the system at the time of release of button 55 was below a certain level, the timer will reset to zero by once again pressing the increase-pressure button 55. As an example, this would occur if the pressure in the system was under two atmospheres. This feature can be helpful in certain balloon preparation procedures.

In still another embodiment, the pressure is increased by holding down the increase-pressure button 55 until the pressure in inflatable member 41 equaled two atmospheres. The increase-pressure button 55 was then released and timer 51 begins timing. The increase-pressure button 55 is then pressed again to increase the pressure in the system to the desired level; e.g., ten atmospheres. The inflation timer 51 continues timing. When the decrease-pressure button 56 is depressed to return the pressure in the system to zero atmospheres, timer 51 automatically stops timing.

In another embodiment, increase-pressure button 55 is depressed and the pressure in the system increases to one atmosphere. Upon release of the increase-pressure button, timer 51 begins timing. If the increase-pressure button is again depressed, the timer will reset to zero and stay there. If the pressure in the system exceeds two atmospheres, increase-pressure button 55 can be depressed any number of times without resetting the inflation timer to zero.

The inflatable member 41 can have a plurality of minute holes 46 for releasing a therapeutic drug into a vessel. In this embodiment of the invention, pressure switch 50 is used to activate inflation device 44 which in turn pressurizes inflation lumen 45 and inflatable member 41. More specifically, increase-pressure button 55 is depressed until a desired pressure is reached in inflatable member 41. At that time, the inflation fluid, which is a therapeutic drug, is released in a controlled manner through minute holes 46 on the surface of inflatable member 41. When increase-pressure button 55 is released, timer 51 begins timing the inflation cycle, and at the same time automatically times the release of the therapeutic drug through hole 46. When the decrease-pressure button 56 is depressed to return the pressure in the system to zero atmospheres, timer 51 automatically stops timing when the pressure in inflatable member 41 reaches zero.

In a further feature of the invention, process control unit 61 is programmed to automatically stop the increase in pressure when the pressure reaches 0 atmospheres from a lower pressure. This is done to facilitate the changing of catheters. For example, upon withdrawal of catheter 40 from the patient, the pressure is normally at a slight negative pressure to keep inflatable member 41 collapsed; e.g., minus one atmospheres. Before catheter 40 has been removed, the physician normally returns the pressure in the system to zero atmospheres so that removal of the used catheter would not occur under negative pressure conditions. In accordance with this aspect of the invention, the physician need merely press increase-pressure button 55 and process control unit 61 will automatically stop the pressure increase at zero atmospheres. The catheter can then be removed and another inserted. Note that in accordance with this feature, the pressure is stopped at zero atmospheres only if it began at a pressure less than zero atmospheres.

The elapsed time of the inflation and deflation cycles is measured by and displayed on timer display unit 70. The timer display unit receives a signal from timer 51 and starts displaying elapsed time on monitor 71 so that the physician and catheter lab personnel can monitor the elapsed time. Timer display unit 70 will stop when timer 51 stops sending a signal at the end of the deflation cycle.

While the invention has been described herein in terms of dilatation catheters and their use in PTCA procedures, the invention can be employed with diagnostic and other types of catheters which are inserted into a body lumen to perform a medical procedure in which it is important to time the procedure. As previously stated, other types of vascular catheters and procedures can be employed, which include fixed wire and rapid exchange systems, drug delivery systems, PTA procedures, and atherectomy procedures, which are known in the art. Other modifications and improvements can be made without departing from the scope of the invention.

What is claimed is:

1. A timing system for measuring the time elapsed during an inflation cycle of a medical procedure, comprising:
   a catheter having a proximal end and a distal end, said proximal end having an inflation device connected thereto, and said catheter having an inflatable member near its distal end;
   an inflation lumen within said catheter providing fluid communication between said inflation device and said inflatable member, said inflation device operable to pressurize and depressurize said inflatable member;
   a timer for measuring elapsed time;
   a manually operable pressure switch operably associated with said inflation device, said pressure switch having an increase-pressure button which is actuated manually to initiate operation of said timer when said increase-pressure button is deactivated; and
   means for displaying the elapsed time so that after said inflation device pressurizes said inflation lumen and said inflatable member with fluid, said timer is manually activated to measure elapsed time during said inflation cycle of the medical procedure.

2. The timing system of claim 1, wherein said timer for measuring elapsed time does not start timing until the pressure in said inflatable member is equal to or greater than atmospheric pressure.

3. The timing system of claim 1, wherein said timer for measuring elapsed time does not begin timing until the pressure in inflatable member exceeds zero atmospheres.

4. The timing system of claim 1, wherein said timer for measuring elapsed time will automatically reset to zero when the pressure in said inflatable member is less than a predetermined pressure level at the time said pressure switch is actuated.

5. The timing system of claim 1, wherein said timer begins to measure time after the pressure in inflatable member equals a predetermined pressure threshold and the pressure switch is deactivated.

6. The timing system of claim 1, wherein said timer resets to zero each time said increase-pressure button is actuated when the pressure in said inflatable member is less than a predetermined pressure threshold.

7. The timing system of claim 1, wherein said timer operates in an analog mode.

8. The timing system of claim 1, wherein said timer operates in the digital mode.

9. The timing system of claim 1, wherein said timer for measuring elapsed time will automatically reset to zero when said increase-pressure button is activated at any pressure level.

10. The timing system of claim 1, wherein said timer for measuring elapsed time will automatically reset to zero when said increase-pressure button is activated at any pressure level below a predetermined pressure threshold.

11. A timing system for measuring the time elapsed during an inflation cycle of a medical procedure, comprising:
   a catheter having a proximal end and a distal end, said proximal end having an inflation device connected thereto, and said catheter having an inflatable member near its distal end;
   an inflation lumen within said catheter providing fluid communication between said inflation device and said inflatable member, said inflation device operable to pressurize and depressurize said inflatable member;
   a timer for measuring elapsed time;

a manually operable pressure switch attached to said inflation device, said pressure switch actuated manually to simultaneously initiate operation of said inflation device to pressurize said inflatable member, said inflation device automatically stopping when the pressure in said inflatable member reaches zero after starting from a negative pressure; and means for displaying the elapsed time so that as said inflation device pressurizes said inflation lumen and said inflatable member with fluid, said timer is manually activated to measure elapsed time during said inflation cycle of the medical procedure.

12. A timing system for measuring the time elapsed during an inflation cycle of a medical procedure, comprising:

a catheter having a proximal end and a distal end, said proximal end having an inflation device connected thereto, and said catheter having an inflatable member near its distal end;

an inflation lumen within said catheter providing fluid communication between said inflation device and said inflatable member, said inflation device operable to pressurize and depressurize said inflatable member;

a timer for measuring elapsed time;

a manually operable pressure switch operably associated with said inflation device, said pressure switch actuated manually to initiate operation of said timer when said pressure switch is deactivated;

a process control unit associated with said pressure switch for controlling the starting and stopping of said timer; and means for displaying the elapsed time so that after said inflation device pressurizes said inflation lumen and said inflatable member with fluid, said timer is manually activated to measure elapsed time during said inflation cycle of the medical procedure.

13. A timing system for measuring the time elapsed during an inflation cycle of a medical procedure, comprising:

a catheter having a proximal end and a distal end, said proximal end having an inflation device connected thereto, and said catheter having an inflatable member near its distal end;

an inflation lumen within said catheter providing fluid communication between said inflation device and said inflatable member, said inflation device operable to pressurize and depressurize said inflatable member with a therapeutic drug;

a plurality of apertures in said inflatable member for controllably dispensing said therapeutic drug;

a timer for measuring elapsed time;

a manually operable pressure switch operably associated with said inflation device, said pressure switch actuated manually to initiate operation of said timer when said pressure switch is deactivated;

a process control unit associated with said pressure switch for controlling the starting and stopping of said timer; and means for displaying the elapsed time so that after said inflation device pressurizes said inflation lumen and said inflatable member with said therapeutic drug, said timer is manually activated to measure elapsed time during said inflation cycle of the medical procedure.

* * * * *